(12) United States Patent
Johnson

(10) Patent No.: US 7,897,587 B2
(45) Date of Patent: Mar. 1, 2011

(54) TOPICAL DERMATOLOGICAL FORMULATIONS AND USE THEREOF

(75) Inventor: Keith A. Johnson, Durham, NC (US)

(73) Assignee: Nycomed US Inc., Melville, NY (US)

( * ) Notice: Subject to any disclaimer, the term of this patent is extended or adjusted under 35 U.S.C. 154(b) by 555 days.

(21) Appl. No.: 10/933,976

(22) Filed: Sep. 3, 2004

(65) Prior Publication Data

US 2006/0052353 A1 Mar. 9, 2006

(51) Int. Cl.
*A61K 31/56* (2006.01)
*C07J 53/00* (2006.01)

(52) U.S. Cl. .................. 514/178; 514/179; 552/500

(58) Field of Classification Search .................. 514/178, 514/179; 552/500
See application file for complete search history.

(56) References Cited

U.S. PATENT DOCUMENTS

| 4,017,615 | A |   | 4/1977  | Shastri et al. ............. 424/241 |
|-----------|---|---|---------|-------------------------------------|
| 4,233,295 | A | * | 11/1980 | Hill et al. .................. 514/174 |
| 4,393,076 | A |   | 7/1983  | Noda et al. ............... 424/317   |
| 5,993,787 | A |   | 11/1999 | Sun et al. .................. 424/59  |
| 6,479,058 | B1 |  | 11/2002 | McCadden ................ 424/401    |
| 6,656,928 | B1 |  | 12/2003 | McCadden ................ 514/167    |
| 6,765,001 | B2 |  | 7/2004  | Gans et al. ................. 514/172 |
| 2002/0032149 | A1 | | 3/2002 | Kensey ........................ 514/1   |
| 2002/0192273 | A1 | | 12/2002 | Buseman et al. ............ 424/449   |
| 2003/0073676 | A1 | | 4/2003 | Biggadike et al. ........... 514/179   |
| 2003/0077316 | A1 | | 4/2003 | Nichols et al. .............. 424/447   |
| 2003/0078517 | A1 | | 4/2003 | Kensey ....................... 600/573   |
| 2003/0149029 | A1 | | 8/2003 | McKew .................... 514/227.8   |
| 2003/0176408 | A1 | | 9/2003 | Gans et al. ................. 514/179   |
| 2003/0186951 | A1 | | 10/2003 | Gans et al. ................. 514/174   |

FOREIGN PATENT DOCUMENTS

| WO | WO 00/24401    | 5/2000 |
| WO | WO02/13868 A1  | 2/2002 |

OTHER PUBLICATIONS

R.B. Stoughton, "Vasoconstrictor Assay-Specific Applications",pp. 42-53, Topical Corticosteroids, Maibach and Surber (eds),Basel 1992.

* cited by examiner

*Primary Examiner*—Sreeni Padmanabhan
*Assistant Examiner*—Kendra D Carter
(74) *Attorney, Agent, or Firm*—Schwegman, Lundberg & Woessner P.A.

(57) ABSTRACT

A topical formulation of an androstane steroid compound of improved solubility in combinations of the solvents propylene glycol and propylene carbonate.

14 Claims, 1 Drawing Sheet

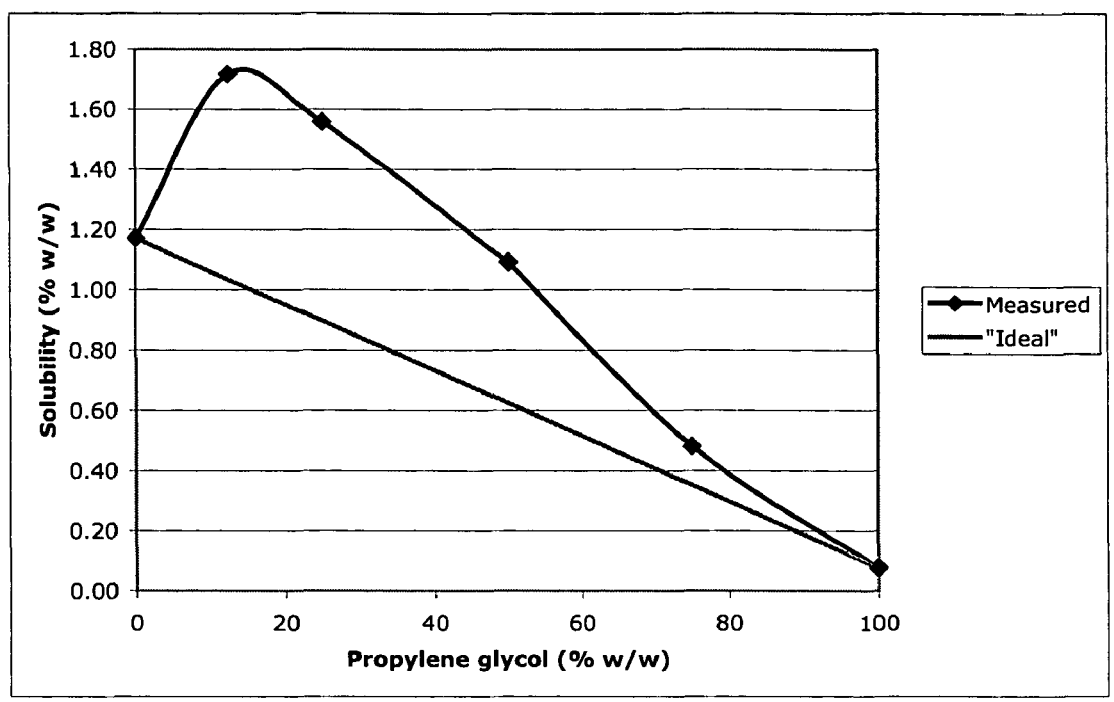

TOPICAL DERMATOLOGICAL FORMULATIONS AND USE THEREOF

FIELD OF THE INVENTION

This invention relates to the field of topical formulations for dermatological uses wherein the formulation has enhanced solubility of the active dermatological agent in the formulation and the use thereof to treat dermatological conditions of a patient. More particularly, this invention relates to the field of topical formulations of androstane steroids, and more particularly esters of fluticasone, for dermatological uses, such as anti-inflammatory and anti-allergic uses, wherein the formulation has enhanced solubility of the active dermatological agent in the formulation and the use thereof to treat dermatological conditions of a patient.

BACKGROUND TO THE INVENTION

Glucocorticosteroids, which have anti-inflammatory and anti-allergy properties, are well known and are widely used to treat conditions requiring an anti-inflammatory and/or anti-allergic response. One such class of glucocorticosteroids having such properties are androstane steroids of the type disclosed in U.S. Pat. No. 4,335,121, and particularly fluticasone esters, and more particularly fluticasone propionate, namely $6_\alpha,9_\alpha$-difluoro-$17_\alpha$(1-oxopropoxy)-$11_\beta$-hydroxy-$16_\alpha$-methyl-3-oxo-androsta-1,4-diene-$17_\beta$-carbothioic acid S-fluoromethyl ester, and derivatives thereof. In this regard, CULTIVATE® topical cream and ointment, containing 0.05% and 0.005% fluticasone propionate respectively, is marketed by GlaxoSmithKline. These products have anti-inflammatory, anti-pruritic and vasoconstrictive properties.

It has been desirable to increase the activity of the active ingredient in such formulations. By increasing the vasoconstrictor potency, the effectiveness of the active ingredient is increased. In International Patent application Publication No. WO 00/24401 it is taught that increased vasoconstrictor potency of fluticasone propionate lotion formulations over fluticasone propionate cream formulations is obtained at decreased concentrations of occlusive agent, i.e., under 10 w/w %. However, it is recognized that the addition of an occlusive agent, such as mineral oil or paraffin, increases the vasoconstrictor potency of topical steroids. Yet, high concentrations of occlusive agents can cause the formulation to be unstable, and invert an oil-in-water emulsion to a greasy feeling water-in-oil emulsion.

In order to still obtain the high vasoconstrictor potency of such a the formulation, while avoiding the instability problem of the product, and still have a relatively high level of occlusive agent in the product, it has been proposed in International patent Publication No. WO 02/13868, to employ a specific type of surfactant system, namely one wherein the surfactant system employed in the formulation must have an HLB value ranging from about 7.0 to about 10.9 and with the surfactant system being present in the formulation in a w/w % amount of from about 0.25 to about 10.0. Also, in United States Patent Application Publication Nos. 2003/0130247 A1, 2003/0176408 A1 and 2003/0186951 A1 it is suggested to employ very high amounts of a penetration enhancer, such as propylene glycol, such that the ratio of the penetration enhancer to a total of the penetration enhancer, solvents and emulsifiers is at lest about 0.70, preferably at least about 0.80 and most preferably about 0.90 or 0.95, so as to obtain enhanced vasoconstriction activity or potency. However, it is desirable to be able to obtain such increased or even better vasoconstriction potency for such androstane-containing topical formulations without the necessity for using such high levels of penetration enhancers.

Thus, there is still a need for better, more reliable topical formulations where the amount of active ingredient available for vasoconstrictor activity is increased and without requiring undue limitations on the compositions of the formulations. Hence, there is a need for such topical formulation where the amount of active ingredient soluble in the solvent system of the formulation is increased and thereby the vasoconstrictor activity or potency of the formulation is increased.

BRIEF SUMMARY OF THE INVENTION

In accordance with the present invention, topical formulations of androstane steroid compounds having increased solubility of the androstane steroid compound in the formulation solvent system is obtained when the solvent system comprises both propylene glycol and propylene carbonate. Thus, the topical formulations of this invention will be a stable formulation comprising an androstane steroid compound in a solvent system comprising both propylene glycol and propylene carbonate. Unexpectedly, it has been discovered that the combination of propylene glycol and propylene carbonate provides a synergistic enhancement of the solubility of the androstane steroid compound in the solvent system. Thus, the formulation provides increased amount of the androstane steroid compound available for vasoconstrictor potency or activity and thereby increased effectiveness of the formulation in treating the dermatological conditions for which the formulation is applied to a patient in need thereof. The androstane steroid compound in the formulation of this invention is a compound of the formula:

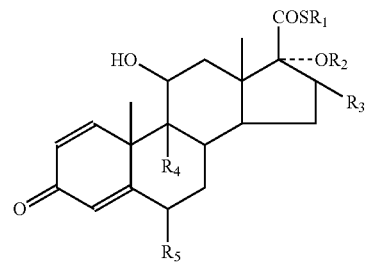

where $R^1$ is a fluoro-, chloro-, bromo-methyl group or a 2'-fluoromethyl group; $R^2$ is a group $COR^6$ where $R^6$ is a $C_{1-3}$ alkyl group or $OR^2$ and $R^3$ together form a $16_\alpha,17_\alpha$-isopropylidenedioxy group; $R^3$ is a hydrogen atom, a methyl group (which may be either the $_\alpha$- or $_\beta$-configuration) or a methylene group; $R^4$ is hydrogen, chlorine or fluorine atom; and $R^5$ is a hydrogen or fluorine atom, and the symbol — represents a single or double bond.

The invention additionally provides a process for topically treating a skin condition of a patient including but not limited to the following conditions, corticosteroid-responsive dermatoses, such as atropic dermatitis, eczema, including atopic, infantile, and disco eczemas, purigo nodularis; neurodermatoses, including lichen simplex, lichen planus, seborrhoeic dermatitis; contact sensitivity reactions; discoid pupus erthematosus; insect bite reactions; prickly heat; inflammation, erythema, papulation, scaling erosion, oozing, crusting, pruritus, impetigo, epidermolysis bullosa, psoriasis, erythema, hidradentis, suppurative warts, diaper rash, jock itch, and combinations of these conditions. The method comprises topically applying a formulation of this invention, as described hereinbefore and hereafter, to a patient in need of the treatment for such a condition. The formulation of this invention will be a topical formulation, generally in a cream or lotion, ointment, or gel form, A further aspect of this invention is a process for the preparation of such formulation of this invention by mixing the androstane steroid active ingredient with the two solvents, propylene glycol and propylene carbonate, and other components of the system including, but not limited to, components such as surfactant(s), stiffening or thickening agent(s), wax(es) as occlusive agent(s), emollient(s), penetration enhancer(s), preservative(s), base(s), and water or buffer, and the like.

BRIEF SUMMARY OF THE DRAWINGS

The invention is illustrated, in part, but not limited by the drawings in which:

the FIGURE is a graph of the theoretical (idealized) and actual solubility of fluticasone propionate in propylene glycol and propylene carbonate and mixtures thereof.

DETAILED DESCRIPTION OF THE INVENTION AND PREFERRED EMBODIMENTS

In accordance with the present invention, topical formulations of androstane steroid compounds having increased solubility of the androstane steroid compound in the formulation solvent system is obtained when the solvent system comprises both propylene glycol and propylene carbonate. Thus, the topical formulations of this invention will be a stable formulation comprising an androstane steroid compound in a solvent system comprising both propylene glycol and propylene carbonate. Unexpectedly, it has been discovered that the combination of propylene glycol and propylene carbonate provides a synergistic enhancement of the solubility of the androstane steroid compound in the solvent. Thus, the formulation provides increased amount of the androstane steroid compound available for vasoconstrictor activity or potency and thereby increased effectiveness of the formulation in treating the dermatological conditions for which the formulation is applied to a patient in need thereof. The androstane steroid compound in the formulation of this invention is a compound of the formula:

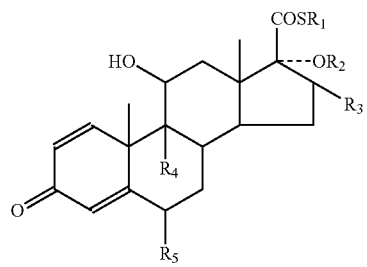

where $R^1$ is a fluoro-, chloro-, bromo-methyl group or a 2'-fluoromethyl group; $R^2$ is a group $COR^6$ where $R^6$ is a $C_{1-3}$ alkyl group or $OR^2$ and $R^3$ together form a $16_\alpha,17_\alpha$-isopropylidenedioxy group; $R^3$ is a hydrogen atom, a methyl group (which may be either the $_\alpha$- or $_\beta$-configuration) or a methylene group; $R^4$ is hydrogen, chlorine or fluorine atom; and $R^5$ is a hydrogen or fluorine atom, and the symbol — represents a single or double bond.

The invention additionally provides a process for topically treating a skin condition of a patient including but not limited to the following conditions, corticosteroid-responsive dermatoses, atopic dermatitis, inflammation, eczema, erythema, papulation, scaling erosion, oozing, crusting, pruritus, impetigo, epidermalysis bullosa, psoriasis, erythema, hidradenitis, suppurative warts, diaper rash, jock itch, and combinations of these conditions. The method comprises topically applying a formulation of this invention, as described hereinbefore and hereafter, to a patient in need of the treatment for such a condition.

A further aspect of this invention is a process for the preparation of such formulation of this invention by mixing the androstane steroid active ingredient with the two solvents, propylene glycol and propylene carbonate, and other components of the system including, but not limited to, components such as surfactant(s), stiffening or thickening agent(s), wax(es) as occlusive agent(s), emollient(s), penetration enhancer(s), preservative(s), base(s) and water or buffer, and the like.

The androstane steroid active ingredient in the topical formulations of this invention is a fluticasone compound or a pharmaceutically acceptable salt or ester thereof. The active ingredient will be present in the topical formulations of this invention in a w/w % amount of from about 0.05 to about 0.50%, preferably from about 0.05 to 0.20%, for cream or lotion and gel formulations, and for ointment formulations the active ingredient w/w % will generally be from about 0.005 to about 0.50% preferably from about 0.005 to 0.20%. The cream and lotion formulations are oil-in-water emulsions, and the ointments are non-aqueous dispersions in a base. Suitable androstane steroid compounds useful as the active ingredient in the formulations of this invention are compounds of the formula:

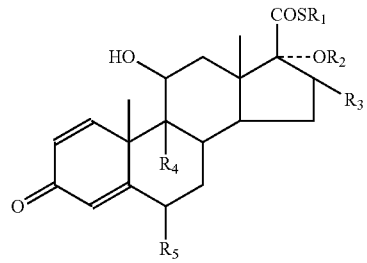

where $R^1$ is a fluoro-, chloro-, bromo-methyl group or a 2'-fluoromethyl group; $R^2$ is a group $COR^6$ where $R^6$ is a $C_{1-3}$ alkyl group or $OR^2$ and $R^3$ together form a $16_\alpha,17_\alpha$-isopropylidenedioxy group; $R^3$ is a hydrogen atom, a methyl group (which may be either the $_\alpha$- or $_\beta$-configuration) or a methylene group; $R^4$ is hydrogen, chlorine or fluorine atom; and $R^5$ is a hydrogen or fluorine atom, and the symbol — represents a single or double bond. The preferred active ingredient is flucatisone propionate.

The solvent system of this invention comprises both propylene glycol and propylene carbonate. The use of both propylene glycol and propylene carbonate as solvents in accordance with this invention permits synergistically increased solubility of the active ingredient in the topical formulations and thereby provides increased vasoconstrictor potency of the formulation based on a given amount of active ingredient in the formulation. The amount of propylene glycol employed in the formulations of this invention will generally be a w/w % amount of from about 2.5 to about 35%. For ointment formulations of this invention the amount of propylene glycol solvent will generally be from about 2.5 to about 7.5 w/w %, for cream or lotion formulations of this invention will generally be from about 2.5 to about 20 w/w %, and for gel formulation of this invention will generally be from about 2.0 to about 35 w/w %. The amount of propylene carbonate employed in the formulations of this invention will generally be a w/w % amount of from about 2.0 to about 20%. For ointment formulations of this invention the amount of propylene carbonate solvent will generally be from about 2.5 to about 7.5 w/w %, for cream or lotion formulations of this invention will generally be from about 2.5 to about 15 w/w %, and for gel formulations of this invention will generally be from about 2.0 to about 20 w/w %. The weight ratio of propylene carbonate to propylene glycol will generally be from about 99:1 to about 1:99, preferably from about 99:5 to about 5:99, more preferably about 99:1 to about 40:60, and still more preferably from about 88:12 to about 45:55, and even more preferably about 88:12.

The topical formulations of this invention may contain a number of other components, including but not limited to, components such as surfactant(s), stiffening or thickening agent(s), wax(es) as occlusive agent(s), emollient(s), penetration enhancer(s), preservative(s), base(s) and water or buffer(s), and the like.

Any suitable compatible surfactant(s) may be employed in the topical formulations of this invention. Examples of such surfactants include, but are not limited to ceteareth-20 available as CETOMACROGOL® 1000, glycerol monostearate, glycerol distearate, glyceryl stearate, polyoxyethylene stearate, a blend of glyceryl stearate and PEG-100 stearate, (As ArLACEL 1 65), polysorbate 40, polysorbate 60, polysorbate 80, CETETH-20®, sorbitan monopalmitate, sorbitan monostearate, sorbitan monooleate, sorbitan sesquioleate, and mixtures thereof. The amount of surfactant(s) employed in the formulations of this invention will generally be in a w/w % of from about 0.5 to about 10%. Generally for the ointment formulations of this invention the amount of surfactant(s) will generally be from about 0.5 to about 5.0 w/w %, and for the cream formulations of this invention the amount of surfactant(s) will be from about 1.0 to about 10 w/w %.

Any suitable occlusive agent may be employed in the topical formulations of this invention. Suitable occlusive agent include, but are not limited to, petrolatum, microcrystalline wax, beeswax, mineral oil, squalene, liquid paraffin, shea butter, carnauba wax, SEPIGEL® (a blend of isoparrafin/polyacrylamide/laureth-7), and mixtures thereof. The occlusive agent is preferably a wax and is present in the formulations of this invention in a w/w % amount of from about 5.0 to about 30%. For the ointment formulations of this invention the occlusive agent or wax component will generally be employed in the formulation in an amount of from about 20 to a bout 30 w/w %, and for cream or lotion formulations of this invention in an amount of from about 5.0 to about 20 w/w %.

Any suitable emollient or skin conditioning agent may optionally be included in the topical formulations of this invention. Suitable emollients include, but are not limited to, cholesterol, glycerine, glyceryl monostearate, isopropyl myristate, isopropyl palmitate, cetostearyl alcohol, lanolin alcohols and mixtures thereof. Optionally, dimethicone, mineral oil or white soft paraffin may also be incorporated into the formulations in relatively small amounts to act as a skin conditioner. The emollient or skin conditioning agent may be present in the topical formulations of this invention in a w/w % amount of from about 0.0 to about 40%. In the ointment formulations of this invention the emollient or skin conditioning agent may generally be present in an amount of from about 0.0 to about 10 w/w %, and in the cream or lotion formulations of this invention may generally be present in an amount of from about 2.0 to about 40.0 w/w %.

The formulations of this invention may also optionally contain any suitable penetration enhancer. Suitable penetration enhancers include, but are not limited to, diethylene glycol, monoethyl ether, n-decyl methyl sulfoxide, dimethyl sulfoxide, dimethylacetamide, laurocapram (Azone®), dimethylformamide, sucrose monooleate, and N-methyl-2-pyrrolidine (Pharmasolve®). The penetration enhancer may be present in the formulations of this invention in an amount of from about 0.0 to about 5.0 w/w %. In the ointment formulations of this invention the penetration enhancer may generally be present in an amount of from about 0.0 to about 5 w/w %, and in the cream or lotion formulations of this invention may generally be present in an amount of from about 0.0 to about 5 w/w %.

The formulations of this invention may also optionally include a buffer or neutralizing agent. Examples of suitable buffers include, but are not limited to, citric acid, lactic acid, oleic acid, sodium phopsphate, water, triethanolamine, sodium citrate, hydrochloric acid and the like. The buffering agent may be present in the composition in any suitable buffering effective a mount. The gel formulation will generally contain a base, such as for example, sodium hydroxide, triethanolamine and the like. The gel formulations of this invention will also generally include a volatile solvent, such as for example, ethanol, isopropanol and the like.

The formulations of this invention may also optionally include preservative or antioxidant components. Examples of such preservative and antioxidant include, but are not limited to, alkyl alcohols, benzyl alcohol, butylated hydroxyanisole, butylated hydroxytoluene, butyl paraben, disodium edetate, citric acid and the like. The preservative and/or antioxidant may be present in the formulations of this invention in a w/w amount of from about 0.0 to about 0.6%, preferably in an amount of from about 0.3 to about 0.6%.

The formulations of this invention optionally may also have present in the formulations thickening or stiffening agent, including but not limited to, dimethicone and polymers. The thickening or stiffening agents may be present in the composition generally in a w/w % amount of from about 0.0 to 10%, preferably from about 0.1 to about 10%, and more preferably in an amount of from about 0.1 to 5%.

Typically ointment formulations of this invention will generally have the following composition components, in the amount indicated.

General Ointment Formulation:

| Component | Approximate Amount (% w/w) |
|---|---|
| Androstane steroid | 0.005 to 0.1 |
| Propylene carbonate[1] | 2.5 to 7.5 |
| Propylene glycol[1] | 2.5 to 15 |
| Surfactant | 0.5 to 1.0 |
| Wax | 20 to 30 |
| Emollient | 0.0 to 10 |
| Penetration enhancer | 0.0 to 5.0 |
| Mineral oil | Q.s. |

[1]The sum of these components is ≦10% w/w.

The androstane steroid is preferably fluticasone propionate.

The ointment formulation will generally be prepared in the following manner. The steroid active ingredient, i.e., fluticasone propionate, will be solubilized in a mixture of propylene carbonate and propylene glycol. The total amount of solvent in these ointment formulations is likely to be 10% w/w or less. This solution will be dispersed in an oil base containing a surfactant and wax. The wax may be a single component or a combination of waxes with different physical properties. Optionally, the formulation may contain an emollient and a penetration enhancer.

Examples of specific ointment formulations of this invention are the following compositions. In these exemplary compositions fluticasone propionate is used as an exemplary androstane steroid, however, it will be recognized that the compositions may contain any androstane steroid.

Ointment Formulation Example 1

| Component | Amount (% w/w) |
| --- | --- |
| Fluticasone propionate | 0.1 |
| Propylene carbonate | 5.0 |
| Propylene glycol | 5.0 |
| Sorbitan sesquioleate | 1.0 |
| Microcrystalline wax | 20 |
| Isopropyl myristate | 5.0 |
| Oleic acid | 2.5 |
| Mineral oil | Q.s. |

Ointment Formulation Example 2

| Component | Amount (% w/w) |
| --- | --- |
| Fluticasone propionate | 0.05 |
| Propylene carbonate | 2.5 |
| Propylene glycol | 2.5 |
| Sorbitan sesquioleate | 0.5 |
| Microcrystalline wax | 20 |
| Isopropyl myristate | 5.0 |
| Oleic acid | 2.5 |
| Mineral oil | Q.s. |

Ointment Formulation Example 3

| Component | Amount (% w/w) |
| --- | --- |
| Fluticasone propionate | 0.1 |
| Propylene carbonate | 5.0 |
| Propylene glycol | 1.7 |
| Sorbitan sesquioleate | 0.75 |
| Beeswax | 25 |
| Oleic acid | 2.5 |
| Mineral oil | Q.s. |

Ointment Formulation Example 4

| Component | Amount (% w/w) |
| --- | --- |
| Fluticasone propionate | 0.05 |
| Propylene carbonate | 2.5 |
| Propylene glycol | 7.5 |
| Sorbitan sesquioleate | 1.0 |
| Microcrystalline wax, 65° C.[1] | 15 |
| Microcrystalline wax, 75° C.[1] | 10 |
| Isopropyl myristate | 2.5 |
| Oleic acid | 2.5 |
| Mineral oil | Q.s. |

[1] Approximate melting point

Further ointment compositions of this invention include, for example, the following compositions, in which the amount of the components are wt %.

| Component | Ointment 5 | Ointment 6 | Ointment 7 | Ointment 8 |
| --- | --- | --- | --- | --- |
| Fluticasone propionate | 0.05 | 0.02 | 0.075 | 0.1 |
| Microcrystalline Wax | 30 | 30 | 30 | 15 |
| Sorbitan sesquioleate | 1.5 | 2 | 3 | 3.0 |
| Glycerol monostearate | 1.5 | 1.5 | 1.5 | 1.5 |
| Oleic acid | 2.5 | 1 | 2.5 | 2.5 |
| Butylated hydroxytoluene | 0.05 | 0.05 | 0.05 | 0.05 |
| Propylene glycol | 0.825 | 3.15 | 1.25 | 3.0 |
| Propylene carbonate | 2.475 | 1.05 | 3.75 | 4.5 |
| Mineral oil | 61.1 | 61.23 | 57.875 | Q.s. |
| Beeswax | — | — | — | 15 |

Typical cream formulation of this invention will generally have the following components in the amounts indicated.
General Cream Formulation:

| Component | Approximate Amount (% w/w) |
| --- | --- |
| Androstane steroid | 0.05 to 0.20 |
| Propylene carbonate[1] | 2.5 to 15 |
| Propylene glycol[1] | 2.5 to 20 |
| Surfactant | 1.0 to 10 |
| Stiffening agent(s) | 0.1 to 14 |
| Waxes | 5.0 to 20 |
| Emollient(s) | 2.0 to 40 |
| Penetration enhancer | 0.0 to 5.0 |
| Mineral oil | 0.0 to 5.0 |
| Preservatives | 0.3 to 0.6 |
| Polymer | 0.0 to 5.0% |
| Base | 0.0 to 5.0% |
| Water (buffer) | Q.s. |

[1] The sum of these components is ≦35% w/w

The androstane steroid is preferably fluticasone propionate.

The cream formulations of this invention will generally be prepared in the following manner. Micronized fluticasone propionate will still be dispersed as fine particles in an oil-in-water cream base that contains propylene carbonate and propylene glycol. The total amount of solvent in these cream formulations is likely to be 35% w/w or less. Optionally, the formulation may contain a penetration enhancer. Drug concentration in the formulation would range from about 0.05 to about 15% w/w.

Exemplary cream formulations of this invention include the following compositions. In these exemplary compositions fluticasone propionate is used as an exemplary androstane steroid, however, it will be recognized that the compositions may contain any androstane steroid.

Cream Formulation Example 1

| Component | Approximate Amount (% w/w) |
| --- | --- |
| Fluticasone propionate | 0.15 |
| Propylene carbonate | 8.0 |
| Propylene glycol | 10 |
| Cetomacrogol ® 1000 | 2.1 |
| Glycerol monostearate | 0.9 |
| Cetosterayl alcohol | 4.0 |
| Beeswax | 8.0 |
| Isopropyl palmitate | 22.0 |
| Oleic acid | 2.5 |
| Parabens/Imidurea | 0.5 |
| Water (buffer) | Q.s. |

Cream Formulation Example 2

| Component | Approximate Amount (% w/w) |
| --- | --- |
| Fluticasone propionate | 0.1 |
| Propylene carbonate | 5.0 |
| Propylene glycol | 5.0 |
| Arlacel ® 165 | 2.5 |
| Polysorbate 60 | 0.5 |
| Cetosterayl alcohol | 4.0 |
| Cetyl esters wax | 5.0 |
| Isopropyl myristate | 20 |
| Oleic acid | 2.5 |
| Mineral oil | 1.0 |
| Dimethicone | 1.0 |
| Parabens/Imidurea | 0.5 |
| Water (buffer) | Q.s. |

Cream Formulation Example 3

| Component | Approximate Amount (% w/w) |
| --- | --- |
| Fluticasone propionate | 0.1 |
| Propylene carbonate | 5.0 |
| Propylene glycol | 10 |
| Cetomacrogol ® 1000 | 2.1 |
| Glycerol monostearate | 0.9 |
| Cetosterayl alcohol | 3.0 |
| Beeswax | 8.0 |
| Isopropyl palmitate | 22.0 |
| Oleic acid | 5.0 |
| Parabens/Imidurea | 0.5 |
| Carbomer 974 | 0.5 |
| Triethanolamine | 0.5 |
| Water (buffer) | Q.s. |

Cream Formulation Example 4

| Component | Approximate Amount (% w/w) |
| --- | --- |
| Fluticasone propionate | 0.1 |
| Propylene carbonate | 10 |
| Propylene glycol | 5 |
| Cetomacrogol ® 1000 | 2.1 |
| Glycerol monostearate | 0.9 |
| Cetosterayl alcohol | 3.0 |
| Beeswax | 8.0 |
| Cetyl wax esters | |
| Isopropyl myristate | 20.0 |
| Oleic acid | 1.0 |
| Parabens/Imidurea | 0.5 |
| Carbomer 974 | 0.5 |
| Sodium hydroxide | 0.25 |
| Water (buffer) | Q.s. |

Cream Formulation Example 5

| Component | Approximate Amount (% w/w) |
| --- | --- |
| Fluticasone propionate | 0.15 |
| Propylene carbonate | 8.0 |
| Propylene glycol | 10 |
| Polysorbate 60 | 1.0 |
| Cetosterayl alcohol | 4.0 |
| Microcrystalline wax | 5.0 |
| Isopropyl palmitate | 5.0 |
| Oleic acid | 5.0 |
| Mineral oil | 10 |
| Parabens/Imidurea | 0.5 |
| Water (buffer) | Q.s. |

Cream Formulation Example 6

| Component | Approximate Amount (% w/w) |
| --- | --- |
| Fluticasone propionate | 0.1 |
| Propylene carbonate | 5.0 |
| Propylene glycol | 5.0 |
| Polysorbate 60 | 1.0 |
| Cetosterayl alcohol | 4.0 |
| Cetyl esters wax | 5.0 |
| Isopropyl palmitate | 5.0 |
| Oleic acid | 2.5 |
| Mineral oil | 20 |
| Parabens/Imidurea | 0.5 |
| Water (buffer) | Q.s. |

Cream Formulation Example 7

| Component | Approximate Amount (% w/w) |
| --- | --- |
| Fluticasone propionate | 0.1 |
| Propylene carbonate | 5.0 |
| Propylene glycol | 10 |

-continued

| Component | Approximate Amount (% w/w) |
|---|---|
| Polysorbate 60 | 2.0 |
| Cetosteryl alcohol | 8.0 |
| Microcrystalline wax | 9.0 |
| Dimethicone | 5.0 |
| Oleic acid | 5.0 |
| Mineral oil | 10 |
| Parabens/Imidurea | 0.5 |
| Water (buffer) | Q.s. |

Cream Formulation Example 8

| Component | Approximate Amount (% w/w) |
|---|---|
| Fluticasone propionate | 0.15 |
| Propylene carbonate | 8.0 |
| Propylene glycol | 5.0 |
| Glycerol monostearate | 3.0 |
| Cetosteryl alcohol | 8.0 |
| Microcrystalline wax | 5.0 |
| Isopropyl palmitate | 5.0 |
| Oleic acid | 5.0 |
| Mineral oil | 10 |
| Parabens/Imidurea | 0.5 |
| Water (buffer) | Q.s. |

Cream Formulation Example 9

| Component | % w/w |
|---|---|
| Fluticasone propionate | 0.1 |
| Beeswax | 10 |
| Isopropyl palmitate | 20 |
| Oleic acid | 1 |
| Dimethicone 20 cs | 1 |
| Cetosteryl alcohol | 3 |
| Glycerol monostearate | 2.1 |
| Cetomacrogol 1000 | 0.9 |
| Propylene glycol | 5 |
| Propylene carbonate | 5 |
| Imidurea | 0.2 |
| Methyl paraben | 0.2 |
| Propyl paraben | 0.1 |
| Carbopol 947P | 0.5 |
| 5% NaOH | 2 |
| Water | Q.s. |

Cream Formulation Example 10

| Component | % w/w |
|---|---|
| Fluticasone propionate | 0.2 |
| Propylene carbonate | 7.5 |
| Propylene glycol | 15 |
| Cetomacrogol ® 1000 | 2.1 |
| Glycerol monostearate | 0.9 |
| Cetosteryl alcohol | 3.0 |

-continued

| Component | % w/w |
|---|---|
| Beeswax | 15 |
| Dimethicone | 0.5 |
| Isopropyl palmitate | 7.5 |
| Isopropyl myristate | 7.5 |
| Oleic acid | 1.0 |
| BHT | 0.05 |
| Parabens/Imidurea | 0.35 |
| Carbomer 974 | 0.5 |
| Sodium hydroxide | 0.15 |
| Water (buffer) | Q.s. |

Typical gel formulations of this invention will generally have the following composition components in the amounts indicated.

General Gel Formulation

| Component | Approximate Amount (% w/w) |
|---|---|
| Fluticasone propionate | 0.05 to 0.2 |
| Propylene carbonate | 2.0 to 35 |
| Propylene glycol | 2.0 to 20 |
| Polymer | 0.1 to 5.0 |
| Base | 0.0 to 5.0% |
| Volatile solvent$^2$ | 0.0 to 30% |
| Water (buffer) | Q.s. |

Examples of specific gel formulations of this invention are the following gel compositions. In these exemplary compositions fluticasone propionate is used as the exemplary androstane steroid, however, it is to be recognized that the composition can contain any androstane steroid.

Gel Formulation Example 1

| Component | Approximate Amount (% w/w) |
|---|---|
| Fluticasone propionate | 0.2 |
| Propylene carbonate | 7 |
| Propylene glycol | 15 |
| Carbomer 974 | 0.5 |
| Sodium hydroxide | 0.25 |
| Water (buffer) | Q.s. |

Gel Formulation Example 2

| Component | Approximate Amount (% w/w) |
|---|---|
| Fluticasone propionate | 0.25 |
| Propylene carbonate | 10 |
| Propylene glycol | 25 |
| Hydroxypropylcellulose | 0.5 |
| Ethanol | 20 |
| Water (buffer) | Q.s. |

Gel Formulation Example 3

| Component | Approximate Amount (% w/w) |
| --- | --- |
| Fluticasone propionate | 0.25 |
| Propylene carbonate | 10 |
| Propylene glycol | 30 |
| Oleic acid | 5.0 |
| Hydroxypropylcellulose | 2.5 |
| Ethanol | 20 |
| Water (buffer) | Q.s. |

The unexpected solubility of the androstane steroid compounds in the combined solvents propylene glycol and propylene carbonate is illustrated by the following solubility data and the solubility graph in FIG. 1 showing the expected idealized or theoretical solubility and the unexpectedly improved solubility actually obtained with the solvent combination of this invention at 25° C. The following Table shows the actual solubility of fluticasone propionate in mixtures of propylene glycol and propylene carbonate.

TABLE

| % propylene glycol/<br>% propylene carbonate | Fluticasone propionate solubility<br>(% w/w) |
| --- | --- |
| 100/0 | 0.08 |
| 75/25 | 0.48 |
| 50/50 | 1.09 |
| 25/75 | 1.56 |
| 12.5/87.5 | 1.72 |
| 0/100 | 1.17 |

In the drawing FIGURE this solubility data obtained at 25° C. is plotted as the dark line and the idealized (theoretical) solubility is plotted as the light line. In "ideal" solutions, the effect of each component is additive in a linear fashion. If solvent A has a property with a value of 50 and solvent B a value of 100 for the same property, an equal blend of A and B would be expected to give a value of 75 for that property. The solubility data obtained with the mixture of propylene glycol and propylene carbonate shows that there is a synergistic solubility effect obtained with this combination of solvents. The lightly colored line represents "ideal" linear behavior. Since propylene glycol can solubilize about 10 times more drug than propylene carbonate, the "ideal" line slopes down strongly as we move from pure propylene glycol to pure propylene carbonate. The darkly colored line shows the actual measured values of fluticasone propionate solubility in the blends. Two important observations can be made. First, for all mixtures, the measured solubility exceeds the ideal solubility. Second, for blends containing about 99 to 45% propylene carbonate, the measured solubility exceeds the solubility in propylene glycol. Both observations are valuable to the formulator because they show that more drug can be incorporated than predicted from the individual contributions of each solvent.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

I claim:

1. An ointment consisting of on a w/w % basis

| Component | % |
| --- | --- |
| Fluticasone propionate | 0.05 |
| Microcrystalline Wax | 30 |
| Sorbitan sesquioleate | 1.5 |
| Glycerol monostearate | 1.5 |
| Oleic acid | 2.5 |
| Butylated hydroxytoluene | 0.05 |
| Propylene glycol | 0.825 |
| Propylene carbonate | 2.475 |
| Mineral oil | 61.1 | and the total of the propylene glycol and propylene carbonate components is about 10% or less.

2. An ointment consisting of on a w/w % basis

| Component | w/w % |
| --- | --- |
| Fluticasone propionate | 0.02 |
| Microcrystalline Wax | 30 |
| Sorbitan sesquioleate | 2 |
| Glycerol monostearate | 1.5 |
| Oleic acid | 1 |
| Butylated hydroxytoluene | 0.05 |
| Propylene glycol | 3.15 |
| Propylene carbonate | 1.05 |
| Mineral oil | 61.23. |

3. An ointment consisting of on a w/w % basis

| Component | w/w % |
| --- | --- |
| Fluticasone propionate | 0.075 |
| Microcrystalline Wax | 30 |
| Sorbitan sesquioleate | 3 |
| Glycerol monostearate | 1.5 |
| Oleic acid | 2.5 |
| Butylated hydroxytoluene | 0.05 |
| Propylene glycol | 1.25 |
| Propylene carbonate | 3.75 |
| Mineral oil | 57.875. |

4. A method for treating a skin condition selected from atopic dermatitis, eczema, erthema, pruritus, impetigo, sporiasis, and inflammation, the process comprising topically applying to the skin a composition of claim 5. A cream composition for topical administration consisting of:
(a) about 0.05-0.2 wt-% fluticasone propionate;
(b) about 2.5-20 wt-% propylene carbonate;
(c) about 2.0-20 wt-% propylene glycol;
wherein the propylene carbonate is about 4.8-95 wt-% of the combination of (b) and (c);
(d) about 1.0-10 wt-% surfactant;
(e) about 2.0-40 wt-% of one or more emollients;
(f) about 5-20 wt-% of an occlusive agent selected from the group consisting of mineral oil, wax and a mixture thereof;
(g) the balance, water;
wherein the cream is an oil-in-water emulsion.

6. The cream of claim 5 wherein the surfactant is ceteareth-20.

7. The cream of claim 5 wherein the occlusive agent is mineral oil.

8. The cream of claim 7 wherein the mineral oil is in the amount of about 1-10 wt-%.

9. The cream of claim 5 wherein the occlusive agent is a mixture of wax and mineral oil.

10. The cream of claim 9 wherein the wax is in the amount of about 5-15 wt-%.

11. The cream of claim 5 wherein the weight ratio of propylene carbonate to propylene glycol in the composition is from about 88:12 to about 45:55.

12. The cream of claim 11 wherein the weight ratio of propylene carbonate to propylene glycol in the composition is about 88:12.

13. A non-aqueous ointment consisting of on a wt/wt % basis
(a) about 0.05-0.2% fluticasone propionate;
(b) about 1-10% of a surfactant selected from the group consisting of sorbitan sesquioleate, glycerol monostearate, sorbitan monostearate, and mixtures thereof;
(c) about 40-75% mineral oil;
(d) about 2.5-7.5% propylene carbonate;
(e) about 2.5-7.5% propylene glycol, wherein the combination of (d) and (e) is about 10% or less;
(f) about 0-0.6% benzyl alcohol, butylated hydroxyanisole, butylated hydroxytolulene, butyl paraben or disodium edetate; and
(g) an effective amount of an occlusive agent consisting of at least one wax.

14. The ointment of claim 13 wherein the wax is in the amount of about 20-30 wt-%.

* * * * *